(12) United States Patent
Berry et al.

(10) Patent No.: US 8,177,755 B2
(45) Date of Patent: May 15, 2012

(54) ACCESS SHEATH WITH CENTRAL SEAL

(75) Inventors: Danny Berry, Hamden, CT (US);
Richard D. Gresham, Guilford, CT
(US); Russell Heinrich, Madison, CT
(US); Patrick Helfrich, Monroe, CT
(US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/763,236

(22) Filed: Apr. 20, 2010

(65) Prior Publication Data

US 2010/0298775 A1    Nov. 25, 2010

Related U.S. Application Data

(60) Provisional application No. 61/180,146, filed on May 21, 2009.

(51) Int. Cl.
*A61M 5/178* (2006.01)
(52) U.S. Cl. .................................. 604/167.03
(58) Field of Classification Search ............. 604/164.01, 604/167.01, 167.02, 167.03, 264, 93.01, 604/158, 164.02, 164.1, 164.11, 192, 198; 606/108
See application file for complete search history.

(56) References Cited

U.S. PATENT DOCUMENTS

| | | | |
|---|---|---|---|
| 5,997,515 A | 12/1999 | de la Torre et al. | |
| 6,416,499 B2 * | 7/2002 | Paul, Jr. | 604/256 |
| 7,563,250 B2 | 7/2009 | Wenchell | |
| 2005/0059934 A1 * | 3/2005 | Wenchell et al. | 604/167.01 |
| 2008/0097332 A1 | 4/2008 | Greenhalgh et al. | |
| 2008/0125716 A1 | 5/2008 | Cruz | |
| 2009/0030375 A1 | 1/2009 | Franer et al. | |
| 2010/0222747 A1 | 9/2010 | Wenchell et al. | |
| 2010/0268162 A1 * | 10/2010 | Shelton et al. | 604/167.01 |

FOREIGN PATENT DOCUMENTS

| | | |
|---|---|---|
| GB | 2 284 452 | 6/1995 |
| WO | WO 2004/096295 | 11/2004 |

OTHER PUBLICATIONS

European Search Report for EP 10 25 0957 date of completion is Aug. 27, 2010 (3 pages).

* cited by examiner

*Primary Examiner* — Christopher D Koharski

(57) ABSTRACT

An access apparatus for use during a surgical procedure to provide access to the interior of the body includes an access member defining a longitudinal axis and having a proximal end for being disposed at an exterior side of the body and a distal end for extending into the interior of the body. The access member has a bore therethrough dimensioned to permit passage of an object. A seal is disposed within the longitudinal bore substantially at the rotational center of the access member. The seal has inner seal portions adapted to establish a substantial seal about a surgical instrument introduced within the longitudinal bore of the access member. An access housing may be mounted to the proximal end of the access member. A zero closure valve may be mounted to the access housing. The zero-closure valve may be adapted to close in the absence of the instrument. The seal may be generally disc shaped. The seal may define an aperture for reception of the surgical instrument. The seal may comprise a fabric material, an elastomeric material or a gel material.

12 Claims, 2 Drawing Sheets

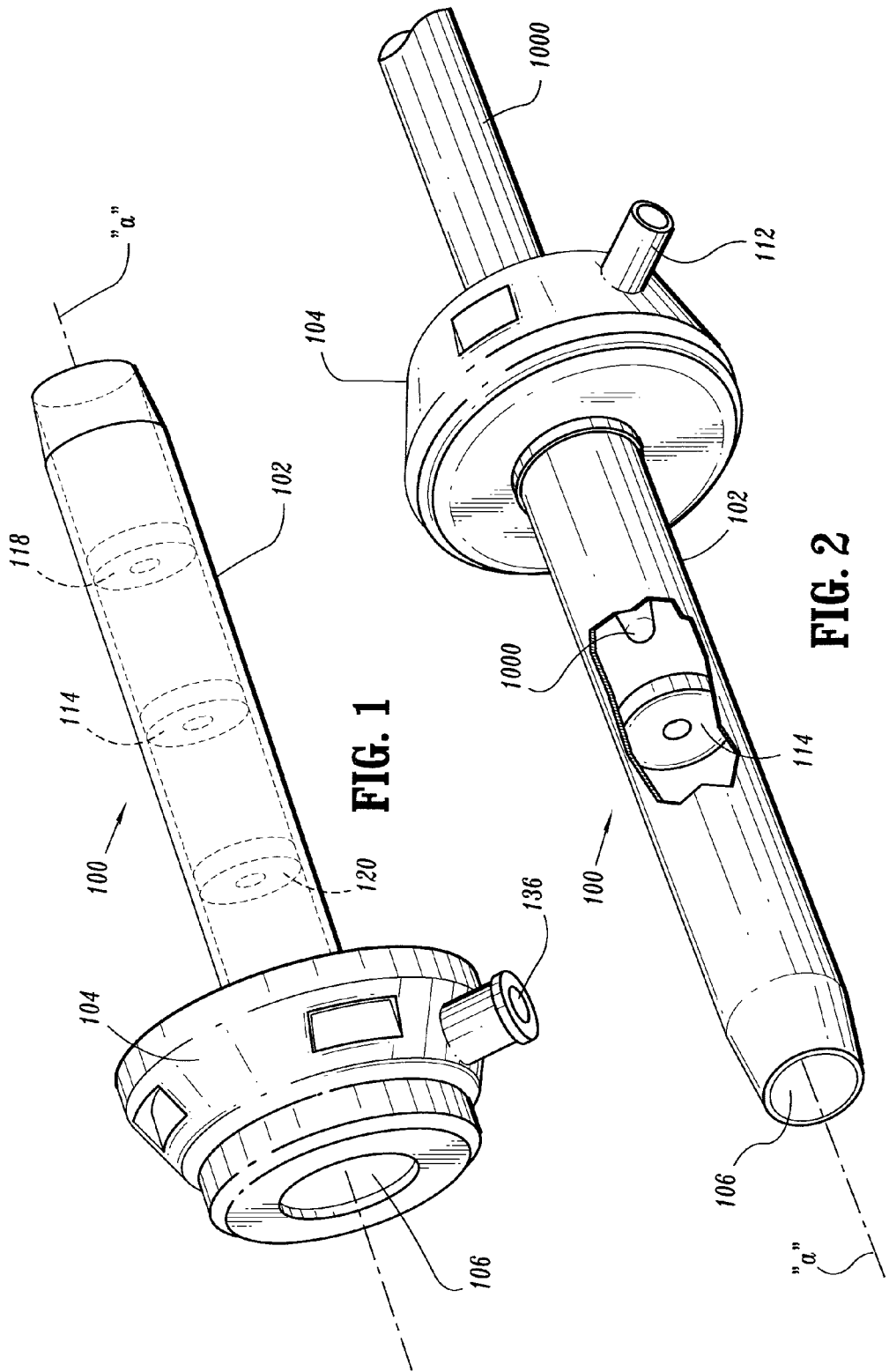

ACCESS SHEATH WITH CENTRAL SEAL

CROSS REFERENCE TO RELATED APPLICATION

The present application claims the benefit of and priority to U.S. Provisional Application Ser. No. 61/180,146 filed on May 21, 2009, the entire contents of which are incorporated herein by reference.

BACKGROUND

1. Field of the Disclosure

The present disclosure relates to surgical devices and, more particularly, to a surgical access apparatus for use during a minimally invasive surgical procedure. The present disclosure further relates to a novel seal assembly for forming a seal about a surgical object while accommodating angular manipulation of the surgical object.

2. Description of the Related Art

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. These procedures typically employ surgical instruments which are introduced into the body through a cannula. The cannula has a housing at a proximal end thereof in which a seal assembly is mounted. The seal assembly provides a substantially fluid tight seal about the instrument to preserve the integrity of the established pneumoperitoneum. The housing extends above the patient's body, when the cannula is inserted into the incision, reducing the effective length of instruments inserted through the cannula and potentially encumbering maneuverability about the operative site.

Minimally invasive procedures have several advantages over traditional open surgery, including less patient trauma, reduced recovery time, reduced potential for infection, etc. However, despite its recent success and overall acceptance as a preferred surgical technique, minimally invasive surgery, such as laparoscopy, has several disadvantages. In particular, the maintenance of the seal about the surgical instrument within the cannula has proven to be difficult in certain procedures, e.g., in procedures requiring extensive manipulation of the long narrow endoscopic instruments within a remote site. In addition, many conventional seal assemblies are not adapted to accommodate instruments of various sizes, while still maintaining the seal about the inserted instrument. Even further, known seal assemblies are relatively complex, which increases the length of the housing in which it is confined. As a consequence, maneuverability above the operative site and the effective length of the instrument are undesirably affected.

SUMMARY

Accordingly, the present disclosure is directed to an access apparatus for use during a surgical procedure to provide access to the interior of the body. The access apparatus includes an access member defining a longitudinal axis and having a proximal end for being disposed at an exterior side of the body and a distal end for extending into the interior of the body. The access member has a bore therethrough dimensioned to permit passage of an object. A seal is disposed within the longitudinal bore substantially at the rotational center of the access member. The seal has inner seal portions adapted to establish a substantial seal about a surgical instrument introduced within the longitudinal bore of the access member. An access housing may be mounted to the proximal end of the access member. A zero closure valve may be mounted to the access housing. The zero-closure valve may be adapted to close in the absence of the instrument. The seal may be generally disc shaped. The seal may define an aperture for reception of the surgical instrument. The seal may comprise a fabric material, an elastomeric material or a gel material.

BRIEF DESCRIPTION OF THE DRAWINGS

Preferred embodiments of the present disclosure will be better appreciated by reference to the drawings wherein:

FIG. 1 is a perspective view of an access apparatus in accordance with an embodiment of the present disclosure;

FIG. 2 is a second perspective view with cut-away portions showing the interior of the cannula of the access apparatus in accordance with the embodiment of FIG. 1;

DETAILED DESCRIPTION OF THE PREFERRED EMBODIMENT(S)

Figure 3:
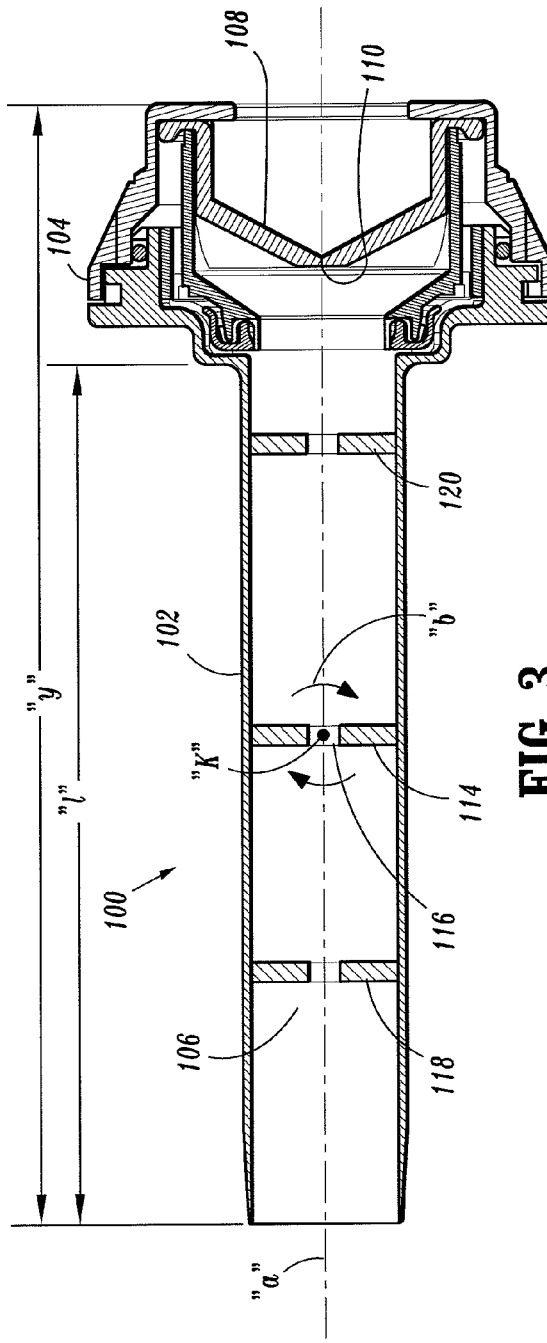
FIG. 3 is a side cross-sectional view of the access apparatus in accordance with the embodiment of FIGS. 1 and 2.

The access apparatus of the present disclosure provides a substantial seal between a body cavity of a patient and the outside atmosphere during insertion of an object through the apparatus. Moreover, the access apparatus of the present disclosure is capable of accommodating objects of varying diameters, e.g., instruments from about 4.5 mm to about 15 mm or more, and provide a gas tight seal with each instrument when inserted. This flexibility of the access apparatus greatly facilitates endoscopic surgery where a variety of instruments having differing diameters are often needed during a single surgical procedure.

The apparatus incorporates a seal which permits the introduction and manipulation of various types of instrumentation adapted for insertion through a trocar and/or cannula assembly while maintaining a substantial fluid tight interface about the instrumentation to preserve the atmospheric integrity of a surgical procedure from gas and/or fluid leakage. Specifically, the seal accommodates angular manipulation of the surgical instrument relative to the seal axis in addition to off-axis manipulation of the surgical instrument. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation".

The access apparatus may also be adapted to receive and Ruin a seal about a physician's aim or hand during a hand-assisted laparoscopic procedure.

Referring now to the drawings, in which like reference numerals identify identical or substantially similar parts throughout the several views, FIGS. 1-2 illustrate an access apparatus in accordance with an embodiment of the present disclosure. For exemplative purposes, the access apparatus will be described in terms of a cannula assembly which is adapted for introduction, typically utilizing a trocar, within the abdominal cavity during a laparoscopic surgical procedure. However, it is appreciated that the access apparatus may be any apparatus suitable for introduction and passage of surgical objects into underlying tissue including, e.g., catheters, trocar assemblies, endoscopic portals, hand access devices, etc., through an incision or through a natural body opening.

Cannula assembly 100 includes a generally tubular member, similar to the conventional cannulas suitable for the intended purpose of accessing a body cavity and permit introduction of instruments therethrough. Cannula assembly 100 is particularly adapted for use in laparoscopic surgery where the peritoneal cavity is insufflated with a suitable gas, e.g., $CO_2$, to raise the cavity wall from the internal organs therein. Cannula assembly 100 is typically used with an obturator assembly, such as a sharp tipped trocar, which is an elongate instrument positionable within the cannula assembly 100. In FIG. 2, an obturator 1000 is shown partially introduced within cannula assembly 100. The obturator assembly 1000 may have a sharp end, a blunt end, or a tapered end for separating or dilating tissue, and is utilized to pass through, e.g., abdominal tissue, to facilitate introduction of the cannula assembly 100 within the abdominal cavity. Once access to the abdominal cavity is achieved, the obturator assembly 1000 is removed from the cannula assembly 100 to permit introduction of the surgical instrumentation utilized to perform the procedure.

In one preferred embodiment, access apparatus, i.e., cannula assembly 100, includes cannula sleeve 102 having proximal and distal ends 101, 103 and cannula housing 104 mounted to the proximal end 101 of the sleeve 102. Cannula sleeve 102 defines a longitudinal axis "a" extending along the length of sleeve 102. Sleeve 102 further defines an internal longitudinal passage 106 dimensioned to permit passage of surgical instrumentation. Sleeve 102 may be fabricated of stainless steel or another suitable rigid material such as a polymeric material or the like. Sleeve 102 may be clear or opaque. The diameter of sleeve 102 may vary, but, typically ranges from 5 to 15 mm. In one preferred embodiment, the connection is achieved through ultrasonic welding, adhesives, cements, etc. In the alternative, the cannula housing 104 and cannula sleeve flange 102 may be connected through a bayonet, threaded or snap-fit coupling, e.g., As best depicted in FIG. 3, a resilient valve 108 is supported within cannula housing 104. Valve 108 may be of general duck-bill configuration and defines an interior slit 110 which opens to permit passage of an object and closes in the absence of the object. The valve 108 is desirably a zero closure valve or a slit seal which is adapted to close in the absence of a surgical object to thereby prevent passage of insufflation gases through cannula assembly 100. In the alternative, valve 108 may be a flat disc-shaped valve, balloon valve, flapper valve, conical valve, etc. Cannula housing 104 desirably includes port 112 for connecting a stop cock to the cannula housing 104. The stop cock connects to an external source of insufflation gases for introducing insufflation gases into the body cavity of the patient through cannula sleeve 102.

Figure 4:
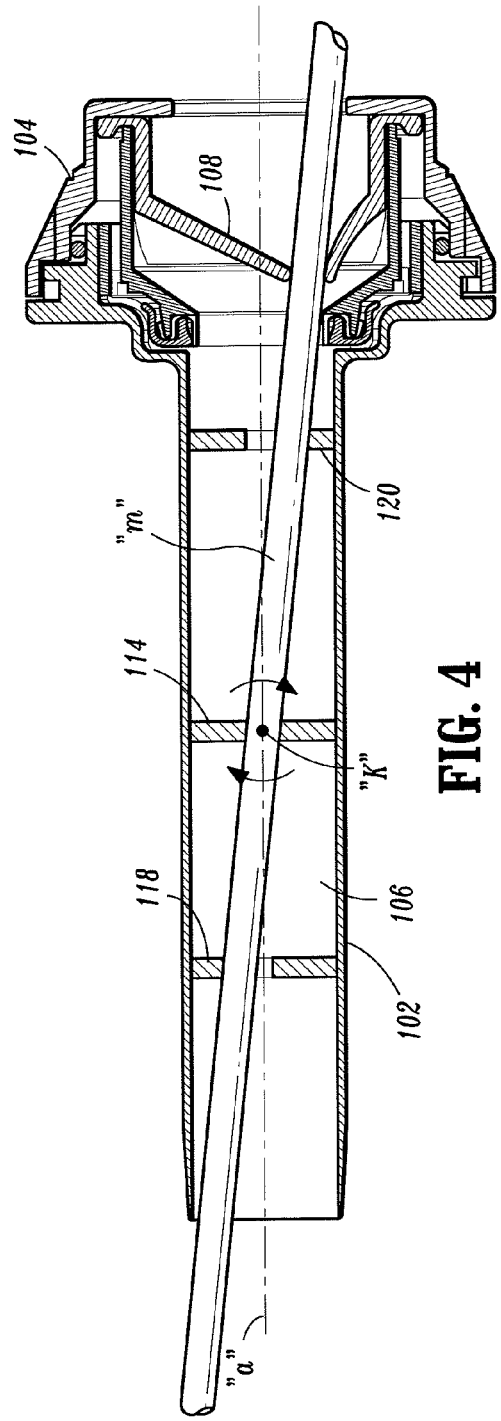
FIG. 4 is a view similar to the view of FIG. 3 illustrating insertion and manipulation of a surgical instrument within the access apparatus with the instrument rotating about a central axis of rotation defined by the access apparatus.

Referring now to FIGS. 3-4, in conjunction with FIGS. 1-2, instrument seal 114 will be discussed. Instrument seal 114 is mounted within sleeve 102 and may be a generally annular or disk-shaped element having inner seal portions defining an internal passage 116 for reception and passage of a surgical instrument in substantial sealed relation. Internal passage 116 may be an aperture, slit or the like adapted to permit a surgical instrument to pass through instrument seal 114. Instrument seal 114 may be mounted within sleeve 102 by any conventional means envisioned by one skilled in the art including, e.g., with the use of adhesives, cements or mechanical mounting means. Instrument seal 114 may comprise any suitable elastomeric material. In one embodiment, instrument seal 114 comprises an elastomeric material, a fabric material, and/or combinations of these materials. The fabric material may comprise braided, woven, knitted, non-woven materials. Instrument seal 114 may be the seal disclosed in commonly assigned U.S. patent application Ser. No. 10/165,133, filed Jun. 6, 2002, the entire contents of which are incorporated herein by reference. The seal disclosed in the '133 application may be a flat septum seal having a first layer of resilient material and a second fabric layer juxtaposed relative to the first layer. In yet a further alternative, instrument seal 114 is preferably a fabric seal and is desirably arranged so as to have a constricted area. The fabric is desirably constructed of a material that forms a constriction or closure. The seal may also be molded with a resilient material so as to have a constriction. Instrument seal 114 they comprise a gel or foam material. Other arrangements for instrument seal 114 are also envisioned.

Instrument seal 114 is preferably disposed at the rotational center "k" of the cannula assembly 100. The rotational center "k" may be at the axial midpoint (the midpoint of the axial length "l") of cannula sleeve 102, or, at the axial midpoint of the combined length "y" of the cannula sleeve 102 and cannula housing 104. The disposition of instrument seal 114 at the rotational center "k" of cannula sleeve 102 or the combined cannula sleeve 102 and cannula housing 104 will enable an inserted surgical instrument "m" to be manipulated through a range of motions as depicted by the directional arrows "b" in FIG. 4 (including angular movement and/or rotational movement) while minimizing distortion of the instrument seal 114. Specifically, the surgical instrument "m" will angulate about the rotational center "k" thereby minimizing the distortion of at least the inner surface portions of instrument seal 114 which is positioned adjacent to or exactly at the location of the rotational center "k". This will thereby preserve the integrity of the seal formed by instrument seal 114 about the surgical instrument "m" and substantially minimize the passage of insufflation gases through the instrument seal 114. In addition, the disposition of instrument seal 114 within cannula sleeve 102 may eliminate the need for cannula housing 104 or, in the alternative, substantially reduce the height requirement of the cannula housing 104 in that the instrument seal 114 does not need to be incorporated within the cannula housing 104.

In other embodiments, second and third instrument seals 118, 120 may be provided along the length of cannula sleeve 102 to provide additional sealing functions. Second and third instrument seals 118, 120 may be similar in construction to instrument seal 114.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical access apparatus for providing access to the interior of the body, which comprises:
an access housing
an access member defining a central longitudinal axis and having a proximal end for being disposed at an exterior side of the body and a distal end for extending into the interior of the body, the proximal end of the access member coupled to the access housing, the access member having a longitudinal bore therethrough dimensioned to permit passage of an object;

a first seal disposed substantially orthogonal to the central longitudinal axis within the longitudinal bore and being substantially at the rotational center of the access member, the seal having a substantially planar profile in the absence of the object and having inner seal portions adapted to establish a substantial seal about a surgical instrument introduced within the longitudinal bore of the access member; and a second seal disposed within the longitudinal bore of the access member, the second seal longitudinally spaced from the first seal.

2. The surgical access apparatus according to claim 1 including a zero closure valve mounted to the access housing, the zero-closure valve adapted to close in the absence of the instrument.

3. The surgical access apparatus according to claim 1 wherein the first seal is generally disc shaped.

4. The surgical access apparatus according to claim 3 wherein the first seal defines an aperture for reception of the surgical instrument.

5. The surgical access apparatus according to claim 1 wherein the first seal comprises a fabric material and an elastomeric material.

6. The surgical access apparatus according to claim 1 wherein a third seal is disposed within the longitudinal bore of the access member.

7. The surgical access apparatus according to claim 6, wherein the third seal is longitudinally spaced from the first seal, and the second seal and the third seal, respectively, being disposed proximally and distally of the first seal.

8. A surgical access apparatus, comprising:

an access member defining a longitudinal axis and including a lumen therethrough, a rotational center of the access member defined by a midpoint of the access member along the longitudinal axis; and at least one seal member disposed within the lumen at the rotational center of the access member, the at least one seal member having an outer diameter and an inner diameter, the inner diameter defining a radially reconfigurable aperture;

the access member having a normal condition in which the aperture of the at least one seal member is partially open;

the access member having a stressed condition in which an object is inserted through the access member, the aperture of the at least one seal member forming a substantially fluid tight seal with the object inserted thethrough;

the outer diameter of the at least one seal member remaining substantially constant during transition between the normal condition and the stressed condition.

9. The surgical access apparatus of claim 8, wherein, in the stressed condition, the at least one seal member maintains a substantially-fluid right seal with the object upon off-axis movement of the object.

10. The surgical access apparatus of claim 8, wherein the outer diameter of the at least one seal member is substantially constant along the longitudinal axis in both the normal and stressed conditions.

11. The surgical access apparatus of claim 8, wherein the at least one seal member is compressed between the inner diameter and the outer diameter in the stressed condition.

12. The surgical access apparatus of claim 8, wherein the seal is coupled to the access member.

* * * * *